US00PP36089P2

(12) United States Plant Patent
Marczyński

(10) Patent No.: US PP36,089 P2
(45) Date of Patent: Sep. 3, 2024

(54) ***CLEMATIS* PLANT NAMED 'BIRTHDAY GIRL'**

(50) Latin Name: *Clematis patens*
Varietal Denomination: BIRTHDAY GIRL

(71) Applicant: Spring Meadow Nursery, Grand Haven, MI (US)

(72) Inventor: Szczepan Marczyński, Pruszków (PL)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 18/387,209

(22) Filed: Nov. 6, 2023

(51) Int. Cl.
*A01H 5/02* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./228
CPC ..... A01H 5/02
See application file for complete search history.

(56) References Cited

PUBLICATIONS

PLUTO UPOVROM Plant Variety Database Citation for 'Birthday Girl' as per PL_O O2151_PBR; Jan. 31, 2022; 1 page.*

* cited by examiner

*Primary Examiner* — Kent L Bell
(74) *Attorney, Agent, or Firm* — Cassandra Bright

(57) ABSTRACT

A new and distinct *Clematis* plant named 'BIRTHDAY GIRL' is disclosed, characterized by semi-double to double flowers blooming from May to July. Distinct pinkish-purple flower color, with a reddish-purple "bar." The new cultivar is a *Clematis* typically suited for ornamental container and landscape use.

2 Drawing Sheets

Figure 1:
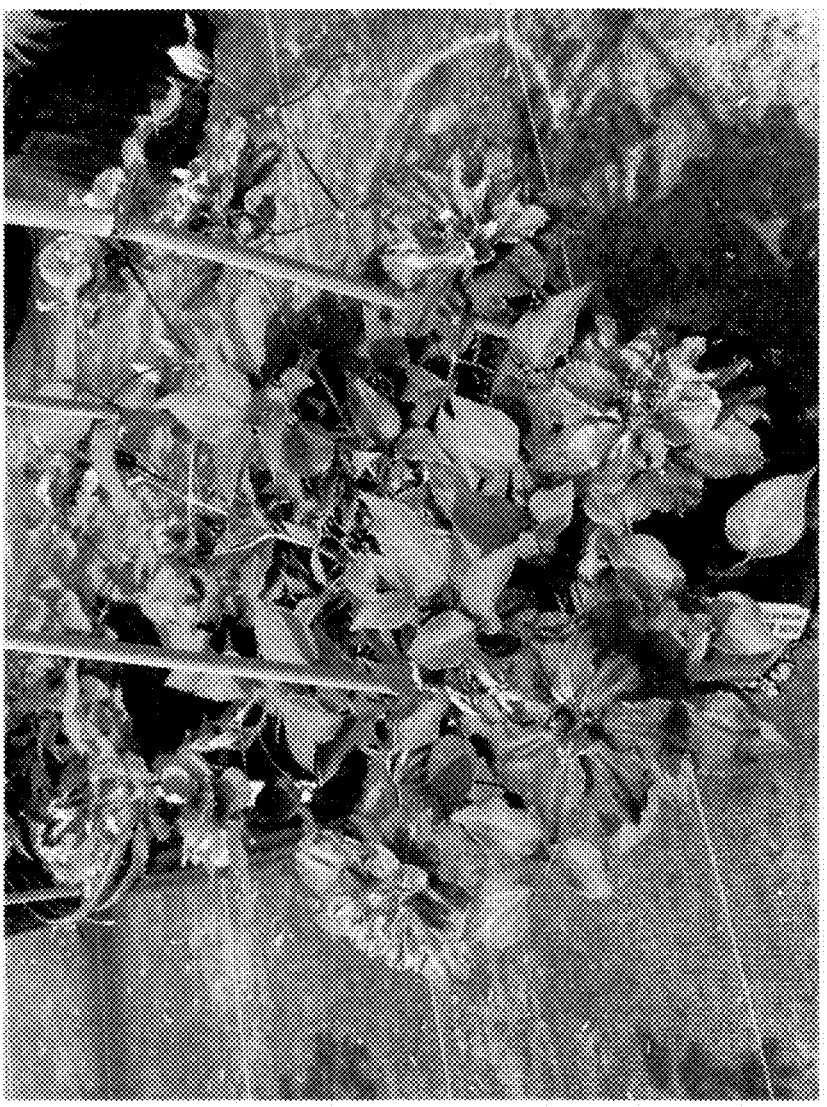

Latin name of the genus and species: *Clematis patens*.
Variety denomination: 'BIRTHDAY GIRL'.

BACKGROUND OF THE INVENTION

The new *Clematis* cultivar is a product of a planned breeding program conducted by the inventor, Szczepan Marczynski, in Pruszkow, Poland. The objective of the breeding program was to produce new *Clematis* varieties with double and semi-double red or pink flowers. The cross resulting in this new variety was made during June of 2013.

The seed parent is the unpatented *Clematis* 'Westerplatte'. The pollen parent is the unpatented *Clematis* 'MAR-12-113-04'. The new variety was identified as a potentially interesting selection in May of 2016 at a greenhouse in Pruszkow, Poland.

Asexual reproduction of the new cultivar 'BIRTHDAY GIRL' by softwood cuttings was first performed during May of 2016, at a greenhouse in Pruszkow, Poland. Subsequent propagation has shown that the unique features of this cultivar are stable and reproduced true to type in 4 successive generations.

SUMMARY OF THE INVENTION

The cultivar 'BIRTHDAY GIRL' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BIRTHDAY GIRL.' These characteristics in combination distinguish 'BIRTHDAY GIRL' as a new and distinct *Clematis* cultivar:

1. Very compact plant growing up to 120 cm in height.
2. Semi-double to double flowers.
3. Pinkish-purple flowers with reddish-purple "bar."
4. Abundant blooming from May to July.

PARENTAL COMPARISONS

Plants of the new cultivar 'BIRTHDAY GIRL' are similar to plants of the seed parent in most horticultural characteristics however, plants of the new cultivar 'BIRTHDAY GIRL' differ in the following:

1. Flowers of the new variety are semi-double to double, while flowers of the seed parent are single.
2. Flower color of the new variety is pinkish-purple with a reddish-purple "bar." Flower color of the seed parent is scarlet.
3. Plants of the new variety are shorter and more compact than plants of the seed parent.

Plants of the new cultivar 'BIRTHDAY GIRL' are similar to plants of the pollen parent, in most horticultural characteristics, however, plants of the new cultivar 'BIRTHDAY GIRL' differ in the following;

1. Flowers of the new variety are semi-double to double, while flowers of the pollen parent are single to semi-double.
2. Flower color of the new variety is pinkish-purple with a reddish-purple "bar." Flower color of the pollen parent is white.

COMMERCIAL COMPARISON

Plants of the new cultivar 'BIRTHDAY GIRL' can be compared to the known commercial variety *Clematis viti-*

*cella* 'Evipo058', U.S. Plant Pat. No. 28,552. The *Clematis* varieties are similar in most horticultural characteristics, including their distinctive pendulous flowers, however, 'BIRTHDAY GIRL' differs from the comparator in the following:

1. Tepal color of the new variety is purplish-pink, while tepal color of this comparator is violet.
2. Flowers of the new variety have more tepals than flowers of this comparator.
3. Tepals of the new variety are more ruffled than tepals of this comparator.
4. Flowers of the new variety are semi-double to double, while flowers of this comparator are single to double.

BRIEF DESCRIPTION OF THE PHOTOGRAPHS

The accompanying photograph in FIG. 1 illustrates in full a typical plant of 'Birthday Girl' in a three-gallon pot, grown outdoors in Pruszkow, Poland. This plant is approximately 2 years old, grown outdoors.

Figure 2:
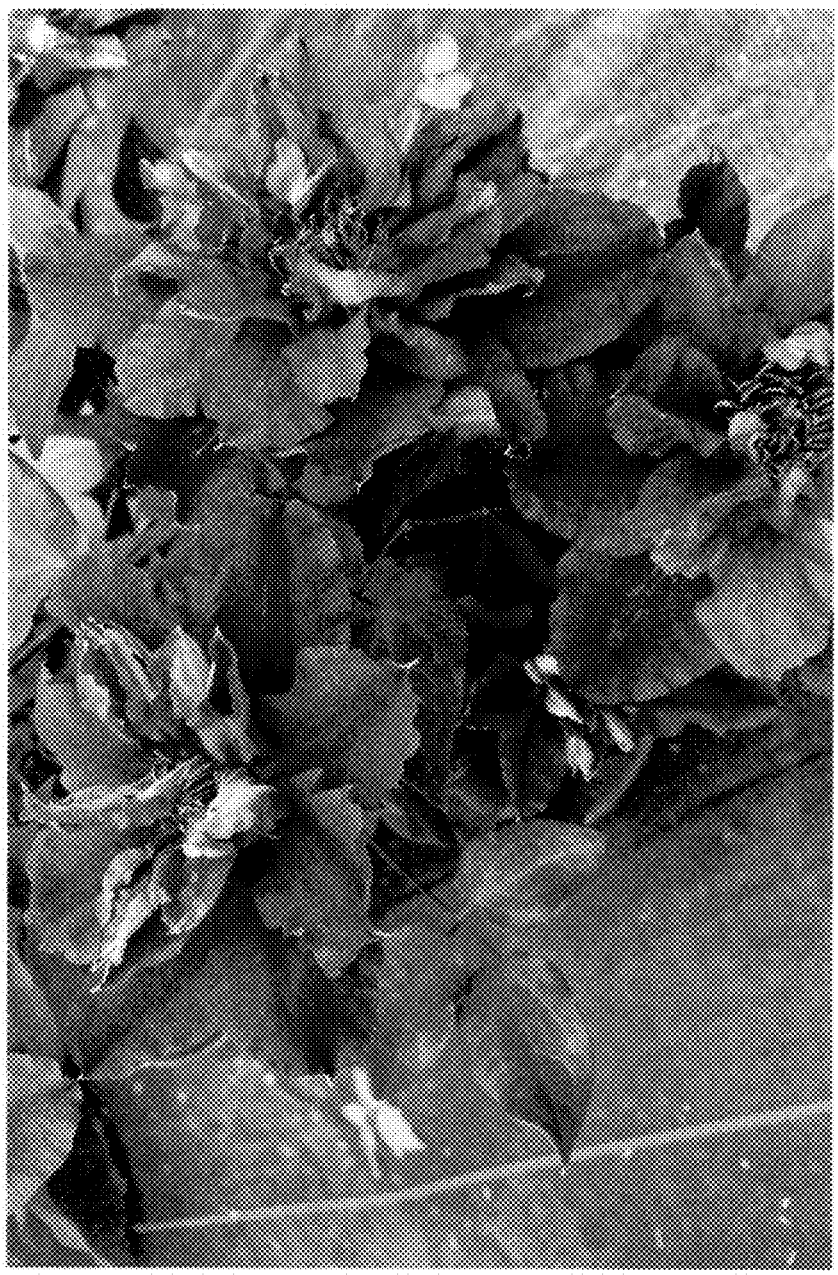

FIG. 2 illustrates a closer view of typical flowers of 'BIRTHDAY GIRL'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'BIRTHDAY GIRL' plants grown in a polyhouse in Grand Haven, Michigan. The growing temperature ranged from approximately 5° C. to 10° C. at night to 18° C. to 27° C. during the day. No artificial light, photoperiodic treatments or chemical treatments were given to the plants. Measurements and numerical values represent averages of typical flowering types. Measurements were taken during May of 2023.

Botanical classification: *Clematis patens* 'BIRTHDAY GIRL'.

Age of the plant described: Approximately 2 years old.

PROPAGATION

Typical method: Softwood cuttings.

Time to initiate rooting: Approximately 10 days at about 18-27° C.

Time to produce a rooted young plant: 20 to 30 days at about 18-27° C.

Root description: Moderately branching, moderately dense, medium thickness, fleshy.

Root color: Light brown, not accurately measured with a color chart.

PLANT

Growth habit: Perennial climbing vine.

Height: 60 cm.

Plant spread: 40 cm.

Plant shape: Upwards and outwards in a vining, climbing, or sprawling manner.

Growth rate: Fast.

Plant vigor: Quite vigorous.

Growth habit: Vining, climbing (though this cultivar is more compact than the typical *Clematis* cultivars known to the inventor).

Quantity of lateral branches: Average 15.

Lateral branch length: 55 cm.

Lateral branch diameter: 2 mm.

Stem:

*Shape.*—Rounded.

*Aspect.*—0° to 90° relative to the ground, depending upon staking and trellising.

*Strength.*—Strong, especially old growth.

*Color.*—Young: RHS Yellow-Green 145B. Mature: Between RHS Greyed-Orange 176A and 166A.

*Texture.*—Pubescence on new growth.

Internode length: 4 to 8 cm.

FOLIAGE

Leaf:

*Arrangement.*—Opposite single and compound trifoliate.

*Compound leaf size.*—

*Length.*—10 cm.

*Width.*—12 cm.

*Leaflet and single leaf.*—

*Length.*—6 cm.

*Width.*—4 cm.

*Shape.*—Ovate.

*Apex.*—Acute.

*Base.*—Cordate.

*Margin.*—Entire.

*Texture.*—Upper Side: Smooth and somewhat fleshy with pubescence around the margins (ciliate). Under Side: Smooth and somewhat fleshy with pubescence around the margins (ciliate), pronounced midrib.

*Color.*—Young foliage upper side: RHS Yellow-Green 146B to 146C. Young foliage under side: RHS Yellow-Green 146D. Mature foliage upper side: RHS Yellow-Green 146B to 146C. Mature foliage under side: RHS Yellow-Green 146D.

*Venation.*—Type: Palmate. Color, upper side: RHS Yellow-Green 145C. Color, under side: RHS Yellow-Green 145C.

Petiole:

*Length.*—2 cm.

*Diameter.*—1.5 mm.

*Texture.*—Both sides lightly pubescent, smooth.

*Color.*—Upper: Between RHS Greyed-Orange 176A and 166A. Lower: Between RHS Greyed-Orange 176A and 166A.

Petiolule:

*Length.*—4 to 7 mm.

*Diameter.*—1 mm.

*Texture.*—Both sides glabrous.

*Color.*—Upper: RHS Greyed-Orange 176A. Lower: RHS Greyed-Orange 176A.

Stipules/tendrils: None.

FLOWER

Natural flowering season: May to July.

Flower type: Rotate, semi-double to double.

Flower arrangement: Single rotate flowers along the lengths of lateral branches, primarily at the apices.

Flowering habit: Freely flowering. Producing 100 to 120 flowers per season. Flowers last on the plant about 2 weeks.

Flower aspect: Upright to outward-facing.

Persistence: Self-cleaning.

Fragrance: None.

Flower size:

*Diameter.*—11 to 13 cm.

*Length.*—11 to 13 cm.

*Depth.*—2 cm.

Bud:

*Shape.*—Ovate.

*Length.*—2 cm.

*Diameter.*—1.5 cm.

*Color.*—RHS Yellow-Green 145B.

Tepals:

*Arrangement.*—Whorl.

*Shape.*—Main Tepal: Broadly elliptic. Smaller Tepal: Narrowly elliptic/oblong.

*Number.*—6 to 8 main tepals with up to 20 smaller tepals.

*Texture.*—Upper Side: Main Tepal: Soft and silky with a velvety medial "bar". Smaller Tepal: Soft and silky, sometimes with a velvety medial "bar" but not as prominent as that of main tepals. Under Side: Main Tepal: Soft and silky. Smaller Tepal: Soft and silky.

*Margin.*—Main Tepal: Entire, but with a distinct "ruffled" quality. Smaller Tepal: Entire, but with a distinct "ruffled" quality and a tendency to fold inward upon itself.

*Tip.*—Main Tepal: Rounded to acute but with a distinct apiculus. Smaller Tepal: Acute/acuminate.

*Base.*—Main Tepal: Attenuate. Smaller Tepal: Attenuate.

*Length.*—Main Tepal: 5.5 cm. Smaller Tepal: 3 cm.

*Width.*—Main Tepal: 3 cm. Smaller Tepal: 1 cm.

*Color.*—When opening: Upper surface: Main Tepal: RHS Violet 83C to 83D with Red-Purple 71A medial "bar". Smaller Tepal: RHS Violet 83C to 83D. Lower surface: Main Tepal: RHS Purple N75A marginally fading to Purple 76B medially. Smaller Tepal: RHS Purple N75A marginally fading to Purple 76B medially. Fully opened: Upper surface: Main Tepal: RHS Violet 83C to 83D with Red-Purple 71A medial "bar". Smaller Tepal: RHS Violet 83C to 83D. Lower surface: Main Tepal: RHS Purple N75A marginally fading to Purple 76B medially. Smaller Tepal: RHS Purple N75A marginally fading to Purple 76B medially.

Petaloids: None.

Peduncle:

*Length.*—2.5 cm.

*Diameter.*—2 mm.

*Strength.*—Strong.

*Angle.*—70° to 90° relative to lateral stem.

*Texture.*—Slightly pubescent.

*Color.*—RHS Yellow-Green 145B, tinted with Purple N77B.

REPRODUCTIVE ORGANS

Stamens:

*Number.*—Average 200 per flower.

*Anther length.*—0.5 cm.

*Anther color.*—RHS Purple N79B.

*Anther shape.*—Linear.

*Filament length.*—1 cm.

*Filament color.*—RHS White NN155B.

*Pollen quantity.*—Moderate.

*Pollen color.*—RHS White 155A.

Pistil:

*Number.*—About 80.

*Length.*—1 cm.

*Style length.*—0.5 cm.

*Style color.*—RHS Yellow-Green 157C.

*Stigma shape.*—Fine, irregular hairs.

*Stigma color.*—RHS Yellow-Green 157C.

*Ovary color.*—RHS Yellow-Green 157C.

OTHER CHARACTERISTICS

Flowers: Flowers may sometimes present as single, especially in summer on new wood growth.

Seeds: Plant has not been proven sterile, but seeds have yet to be observed.

Disease/pest resistance: Neither resistance nor susceptibility to normal diseases and pests of *Clematis* has been observed.

Temperature tolerance: −31° C. to 38° C.

What is claimed is:

1. A new and distinct cultivar of *Clematis* plant named 'BIRTHDAY GIRL' as herein illustrated and described.

* * * * *